United States Patent

Bassett et al.

Patent Number: 5,925,796
Date of Patent: Jul. 20, 1999

[54] METHOD TO DE-COUPLE METHYL ISOBUTYL KETONE AND DIISOBUTYL KETONE CO-PRODUCED FROM ACETONE AND/OR ISOPROPYL ALCOHOL

[75] Inventors: Mark Robert Bassett; Brian Terry Keen, both of Charleston, W. Va.

[73] Assignee: Union Carbide Chemicals & Plastics Technology Corporation, Danbury, Conn.

[21] Appl. No.: 08/932,186

[22] Filed: Sep. 16, 1997

[51] Int. Cl.$^6$ .................................................. C07C 45/72
[52] U.S. Cl. ........................ 568/388; 568/390; 568/391
[58] Field of Search ................................. 568/396, 391, 568/881, 388, 390

[56] References Cited

U.S. PATENT DOCUMENTS

| | | | |
|---|---|---|---|
| 3,379,766 | 4/1968 | Hwang et al. | 260/593 |
| 3,657,351 | 4/1972 | Araki et al. | 260/593 |
| 4,704,478 | 11/1987 | Olson | 568/388 |
| 4,704,480 | 11/1987 | Gefri et al. | 568/396 |

FOREIGN PATENT DOCUMENTS

| | | |
|---|---|---|
| 48/13086 | 7/1973 | Japan . |
| 52/15575 | 4/1997 | Japan . |
| 64150 | 5/1974 | Romania . |
| 656405 | 8/1951 | United Kingdom . |
| 1116037 | 6/1968 | United Kingdom . |
| 1183664 | 3/1970 | United Kingdom . |

*Primary Examiner*—Gary Geist
*Assistant Examiner*—Sreeni Padmanabhan
*Attorney, Agent, or Firm*—Gerald L. Coon

[57] ABSTRACT

A method for the catalytic manufacture of MIBK and DIBK from DMK and/or IPA (optionally in the presence of water) while obtaining improved control over the ratio of DIBK to MIBK in the product stream, comprising reacting, in the presence of an aldol condensation catalyst, a reactant mixture comprising DMK and/or IPA and an effective amount of an additional reactant selected from the group consisting of mesityl oxide (MSO) and methyl isobutyl carbinol (MIBC) and mixtures thereof. Reaction temperature may also be changed to affect the product ratio obtained. The preferred catalyst is copper-based. An overall excess of hydrogen is desired, and this may be achieved by introducing or recycling hydrogen, and/or by balancing exothermic and endothermic reactions. By this invention, the product ratio of DIBK to MIBK is altered such that, as DMK and/or IPA conversion is increased, a lesser amount of DIBK than normal is produced, resulting in improved ability to control the product ratio of these materials.

17 Claims, 1 Drawing Sheet

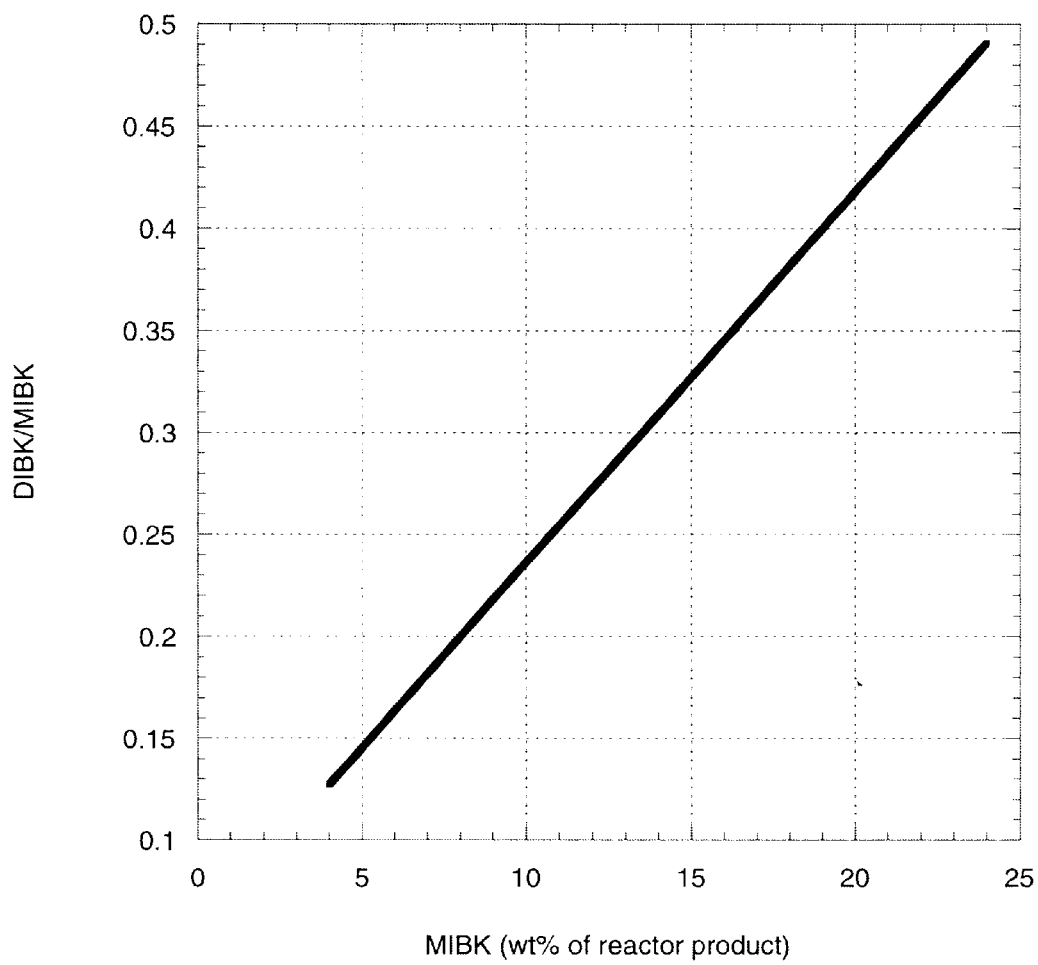

METHOD TO DE-COUPLE METHYL ISOBUTYL KETONE AND DIISOBUTYL KETONE CO-PRODUCED FROM ACETONE AND/OR ISOPROPYL ALCOHOL

FIELD OF THE INVENTION

This invention relates to the production of methyl isobutyl ketone (MIBK) and diisobutyl ketone (DIBK) by the catalytic reaction of acetone (DMK) and/or isopropyl alcohol (IPA). More specifically, this invention relates to a method for controlling the ratio of MIBK to DIBK produced.

SUMMARY OF THE PRIOR ART

MIBK and DIBK are well-known derivatives of acetone, and are often co-produced by the catalyzed reaction of DMK and/or IPA. Typically, an aldol condensation catalyst is used, a preferred embodiment of which is based on copper.

MIBK and DIBK occur in the output of such processes in a natural ratio to each other; however, this ratio is not constant, i.e., the ratio of DIBK to MIBK increases as steps are taken to increase MIBK production. This phenomenon is illustrated by the FIGURE, showing an empirically determined, fitted line which depicts the DIBK/MIBK ratio as a function of the MIBK produced. Unfortunately, the needs of the marketplace do not necessarily conform to the natural tendencies of the chemistry. Thus, as will be readily appreciated from the FIGURE, if it is desired to increase the MIBK production to meet market demands, an excessive amount of DIBK may be produced, resulting in the need to store or destroy some of the DIBK, and to accept the related raw material inefficiencies and energy penalties. Accordingly, it would be very desirable to have a method whereby the DIBK/MIBK ratio is readily controlled, permitting the manufacturing operation to, in effect, "dial in" the amount of either material desired and also obtain a more desired amount of the other material, thereby "de-coupling" the usual relationship between the production levels of these two products. The present invention provides such a method.

BRIEF DESCRIPTION OF THE FIGURE

The FIGURE illustrates the approximate DIBK/MIBK ratio typically occurring at given MIBK production rates.

SUMMARY OF THE INVENTION

The present invention provides a method for the catalytic manufacture of MIBK and DIBK from DMK and/or IPA (optionally in the presence of water) while obtaining improved control over the ratio of DIBK to MIBK, comprising reacting, in the presence of an aldol condensation catalyst, a reactant comprising DMK and/or IPA (optionally in the presence of water), and an effective amount of an additional reactant selected from the group consisting of mesityl oxide (MSO) and methyl isobutyl carbinol (MIBC), and mixtures thereof. By the expression "effective amount" is meant an amount which results in a deviation in the DIBK/MIBK ratio from that shown in the FIGURE. Preferably, such deviation will be at least about 5%, more preferably at least about 10%. Reaction temperature may be increased or decreased, as desired, to effect a desired increase or decrease, respectively, in conversion of DMK and/or IPA and correspondingly the DIBK/MIBK ratio.

The invention further comprises a method for the catalytic manufacture of MIBK and DIBK from DMK and/or IPA, optionally in the presence of water, while obtaining improved control over the ratio of DIBK to MIBK, comprising reacting, in the presence of an aldol condensation catalyst, a reactant comprising DMK and/or IPA, and an effective amount of an additional reactant selected from the group consisting of mesityl oxide (MSO), methyl isobutyl carbinol (MIBC), and mixtures thereof, and further comprising decreasing or increasing the aldol condensation reaction rate by decreasing or increasing the reaction temperature.

DESCRIPTION OF THE INVENTION

Without intending to be bound to any particular chemical theory, it is believed that the co-production of MIBK and DIBK from IPA and/or DMK involves the following reactions:

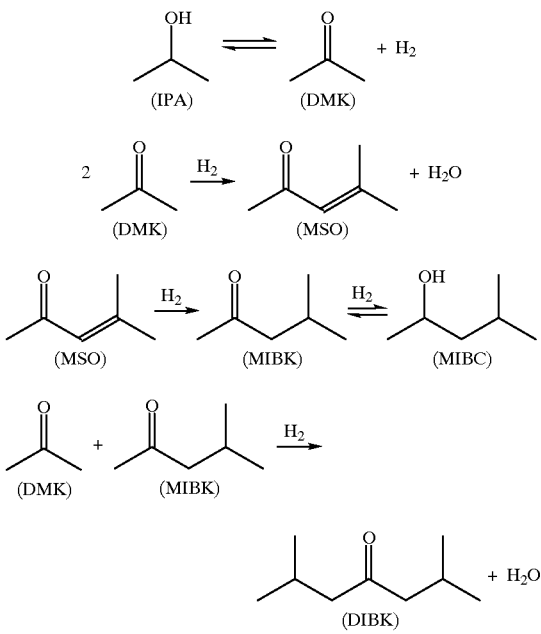

It may be noted that isomers of MSO and DIBK exist and are probably present in the chemical mix; however, they are not believed to be significant to the instant invention, and are considered herein as normal MSO and DIBK, respectively.

In accordance with the invention, MSO or MIBC or mixtures thereof, derived from sources external to the process or optionally from appropriate recycle streams of the process, are co-fed to the reactor along with the usual DMK and/or IPA and optionally water. While it is contemplated that the MSO and/or MIBC used as the co-feed in the instant invention will be provided from sources external to the process, the MSO and/or MIBC produced within the overall reaction chemistry outlined above can also be exploited in determining the desired quantities of those reactants needed to practice the instant invention.

It has been surprisingly found that the addition of supplemental MSO and/or MIBC, when properly controlled, along with the proper control of temperature, as will be discussed more fully below, results in predictable and favorable control of the DIBK/MIBK ratio. Otherwise stated, the DIBK/MIBK ratio can now be influenced such that a lesser amount of DIBK is produced per unit of MIBK than is shown in the FIGURE. This permits the manufacturing operators to select the desired production level of one or the other of those products without having the level of the other product inherently dictated.

Either MSO or MIBC or mixtures thereof with each other or with other reactants in the system can be co-fed at concentrations of up to at least about 20% or more by weight of the total inlet stream to the reactor, including the DMK, IPA and water if present. As will be understood by those skilled in the art, a reasonable degree of experimentation may be desired in order to obtain satisfactory operating results in any given manufacturing system. Optimization of the relevant concentrations are considered to be within the skill of the art, and will, of course, depend upon local operating conditions, such as the ability of the reaction system to remove heat and externally supply hydrogen. Preferably, at least one of MSO or MIBC will be present in the inlet stream in a concentration of at least about 2% by weight, more preferably at least about 5% by weight.

As has been noted, a desired increase in the level of MIBK had previously resulted in an excessive increase in the level of DIBK. Since MSO and MIBC are readily converted to MIBK in the catalytic reaction, it would have been expected that feeding additional MSO and/or MIBC would have resulted in excessive DIBK. It is another surprising result of the instant method that such an increase in DIBK does not occur, i.e., that the DIBK/MIBK ratio expressed in the FIGURE has been favorably altered. Manipulating the reaction temperature could further alter this ratio, and is an important option in the application of this invention.

It will also be readily noted that MSO is a byproduct of the process; thus, it is a surprising feature of the present invention that external MSO could be fed to the process without resulting in an excess thereof in the products. MSO typically occurs in the product mix at concentrations of about 0.5 weight percent or less, and is particularly found as an impurity in MIBK because its boiling point is close to that of MIBK. Accordingly, it is a surprising advantage of the present invention to avoid producing MSO at significantly higher rates, and preferably even less than, those of the prior art processes. In fact, it has been found that even as much as about 20% additional MSO by weight of total feed mixture can be co-fed without experiencing an increase in MSO in the product stream. As a rough approximation, it can be said that in a typical converter for which IPA is the raw material about one pound of MSO and/or MIBC can be fed for each pound of DMK that is made in the converter, and that about 90% or more of the MSO and/or MIBC will be consumed in the production of MIBK and DIBK. It should also be noted that changing the temperature will also change the DIBK/MIBK ratio, as discussed more fully below.

As is apparent from the reaction chemistry outlined above, hydrogen is both a product and a reactant in the system. It is preferred that an excess of hydrogen be maintained throughout. This condition is conveniently referred to as the hydrogen balance. As will be recognized by those skilled in the art, the desired hydrogen level can be achieved by such process means as feeding fresh hydrogen, or recycling unused or produced hydrogen.

In addition, the system has a certain ability to remove heat. This condition is conveniently referred to as the heat balance. If an excessive amount of MSO is fed to the system, the exothermic reaction between MSO and hydrogen will give off an excessive amount of heat, deactivation of the catalyst may occur, and the consumption of hydrogen will be excessive. Thus, typically, a manufacturing unit is limited in how much MSO can be fed without disrupting the hydrogen balance and/or the heat balance to such an extent that the result is unacceptable.

It will be appreciated that better control of the reaction will be achieved if the overall system is kept within an acceptable heat balance. Thus, it is desirable to take into account the stoichiometry of the reactions mentioned above, as well as the relevant heats of reaction. For a system which has only IPA as a raw material, the rule of thumb for an ideal, adiabatic system is that a pound of MSO can be fed for every pound of DMK that is made by the system. This is because the heat for the production of DMK is about the same amount endothermic as the hydrogenation of MSO to MIBK is exothermic. This also maintains the hydrogen in excess because one pound/hour of DMK production makes about 0.02 pound/hour hydrogen, while MSO hydrogenation of one pound/hour consumes about 0.01 pound/hour. Most systems are not ideal, of course, so it may be possible to successfully feed more MSO than would be suggested by the foregoing analysis.

According to the instant invention, it has been found that concerns about feeding excessive MSO can be alleviated by limiting MSO input to the concentration levels discussed herein, and/or by using a mixture of MSO and MIBC. Since the reaction of MSO with hydrogen gives off about 460 Btu/lb MIBK and the conversion of MIBC to MIBK takes in about 250 Btu/lb MIBK, it is apparent that the exotherm generated by the MSO reaction can be mitigated by diluting the MSO with MIBC to increase the endotherm of that reaction. Selection of the optimum ratio will, or course, be a matter of routine calculation and experimentation within the skill of the art.

While a bi-functional copper-based aldol condensation catalyst also capable of carrying out hydrogenation/dehydrogenation chemistry is preferably used in the present method, the beneficial effects of the invention, as described above, are not considered to be dependent on any specific catalyst composition. Accordingly, the present invention should be understood as applicable to any catalyst useful for the production of MIBK and/or DIBK from IPA and/or DMK. Included among such catalyst are those based upon Pd, ZnO, Cu chromite, and Al/Mg/Zn/Ni mixtures. Such catalysts often have one or more base metals (e.g., Na, Ca, Mg, Li, and the like) for the condensation chemistry, in combination with one or more metals such as Cu, Cr, Ni, Pd or Zn, and the like, for the hydrogenation/dehydrogenation chemistry. The preferred catalyst, however, as used in the Examples below, comprises about 10% Cu, about 1% Ca, and about 0.5% Cr by weight of the metal, the remainder being the support, preferably alumina. For purposes of the present invention, the composition of the catalyst is not believed to be narrowly critical. For example, the concentration of the hydrogenation catalyst (e.g., Cu, Cr, Ni, etc.) may be about 5 to about 15% by weight, while the concentration of the base metal (e.g., Ca, Na, Mg, etc.) may be in the range of about 0.5 to about 3% by weight. With respect to the preferred catalyst composition described above, the Cr is optional, and may range from 0 to about 1%.

Except as will be discussed below in connection with the change of temperature to enhance control over the DIBK/MIBK ratio, choice of reaction temperature, within the temperature operating envelope of the chosen catalyst, is not narrowly critical, and can typically range from about 150° to about 300° C., preferably about 180° to about 270° C., more preferably about 200° to about 260° C. Temperatures above about 270° C., depending upon the thermal stability of the specific catalyst in use, are preferably avoided in order to minimize deactivation of the catalyst. Obviously, lower temperatures are preferred for that reason. Also, as temperature increases, equilibria begin to drive the hydrogenation reactions toward MSO, making the concentration of MSO increase.

Choice of reaction pressure is not narrowly critical. Operation in the range of about 10 to about 30 psig is suggested.

Similarly, flow rate through the reactor is not narrowly critical, and may typically range from about 0.1 to at least about 10.0 LHSV, preferably from about 0.1 to at least about 3.0 LHSV. By the term "LHSV" is meant liquid hourly space velocity, a commonly used measure which equals the volumetric rate of feed in the liquid state per volume of catalyst. (As used in the Examples below, it should be pointed out that although the measurement of LHSV is made at atmospheric pressure and in the liquid state, the reaction was run in the gas phase and at pressure.) Preferably, the flow rate will be in the range of about 0.5 to about 1.5 LHSV, and more preferably in the range of about 0.75 to about 1.25 LHSV.

As has been mentioned, temperature increases or decreases may be imposed upon the reaction in combination with the use of the MSO and/or MIBC co-feed as a means to obtain further control of the DIBK/MIBK ratio; thus, this invention also shows that manipulating temperature in conjunction with MSO/MIBC co-feed can further improve the unit's ability to produce a wide range of DIBK/MIBK ratios. As a theoretical example, suppose the system were under typical operating conditions and feed composition, and the system would thus produce 13% MIBK and 4% DIBK. Now replace 10 wt % of the feed with MSO. The system might then produce 20% MIBK and 6.5% DIBK. Historically, to reach 20% MIBK, the system would have produced 8.5% DIBK; therefore, approximately a 25% relative reduction in DIBK was obtained. If the temperature in the above theoretical example (i.e., typical operating conditions and with 10% MSO in the feed) is decreased 15° C., the system might produce 17% MIBK and 4% DIBK. Historically, to reach 17% MIBK, the system would have produced 6% DIBK; therefore, approximately a 33% relative reduction in DIBK was obtained. Surprisingly, by co-feeding MSO and altering temperature, MIBK was increased 30% without increasing DIBK, as compared to the example with typical reactor conditions and feed composition. Further manipulation of MSO/MIBC co-feed and temperature could lead to increased MIBK production with decreased DIBK production.

Without intending to be bound to any particular chemical theory, a reasonable explanation for the result is as follows. The hydrogenation/dehydrogenation reactions occur readily over the entire temperature range of operation. The condensation reactions are very temperature-dependent. Therefore, whatever MSO/MIBC is fed readily produces MIBK. However, if the temperature is sufficiently lowered, the condensation reaction of MIBK with DMK to form DIBK is significantly reduced.

EXAMPLES

The examples which follow are intended to illustrate the invention, but not to limit it in any way.

Example 1

Approximately 170 cc/hr (LHSV=0.85) of a mixture which was ~45%/45%/10% by weight DMK/IPA/H$_2$O was fed to 200 cc of a Cu-based catalyst at 220° C. and 20 psig. The reactor product contained ~13.5 wt % MIBK and 4.4 wt % DIBK (DIBK/MIBK=0.33). With all other reactor conditions being the same, the feed mixture was changed to 39%/39%19%/13% DMK/IPA/H$_2$O/MSO. The reaction product contained ~22.5% MIBK and 8.1 wt % DIBK (DIBK/MIBK=0.36). From the data shown in the FIGURE, the DIBK which would have resulted from running the system at higher IPA/DMK conversion would have been 10.1%. Therefore, a 20% relative reduction in DIBK production was obtained by co-feeding MSO. There was essentially no increase in the amount of MSO leaving the reactor.

Example 2

Approximately 150 cc/hr of a mixture which was ~45%/45%/10% DMK/IPA/H$_2$O was fed to 200 cc of a Cu-based catalyst at 220° C. and 20 psig. The reactor product contained ~14.1 wt % MIBK and 4.4 wt % DIBK (DIBK/MIBK=0.29). With all other reactor conditions being the same, the feed mixture was changed to 40%/40%/10%/10% DMK/IPA/H2O/MIBC. The reaction product contained ~18.7% MIBK and 5.4 wt % DIBK (DIBK/MIBK=0.28). From the data shown in the FIGURE, the DIBK which would have resulted from running the system at higher IPA/DMK conversion would have been 7.3%. Therefore, an ~25% relative reduction in DIBK production was obtained by co-feeding MIBC.

Example 3

Example 2 was carried further with a decrease in temperature to 210° C. The reaction product contained 14.3% MIBK and 2.2% DIBK. Therefore, by co-feeding MIBC and lowering temperature, MIBK production was maintained, as compared to the base case of Example 2, while decreasing DIBK production by about 50%.

Example 4

Example 1 was carried forward with the feed mixture now containing 36%/36%/10%/18% DMK/IPA/H$_2$O/MSO. The catalyst now had operated an additional week and had undergone some deactivation, which is similar in effect to lowering the temperature. The reactor product now contained 25% MIBK and 5% DIBK (DIBK/MIBK=0.2). From the data shown in the FIGURE, the DIBK which would have resulted from running the system at higher IPA/DMK conversion would have been 12.6%. Therefore, an ~60% relative reduction in DIBK production was obtained by co-feeding MSO and effectively lowering the reaction temperature. In fact, as compared to the base case in Example 1, the MIBK production had been increased by about 85% without significantly increasing DIBK production.

Example 5

Approximately 190 cc/hr (LHSV=0.95) of a mixture which was ~45%/45%/10% DMK/IPA/H$_2$O was fed to 200 cc of Cu-based catalyst at 250° C. and 20 psig. The reactor product contained 10.5 wt % MIBK and 2.2 wt % DIBK (DIBK/MIBK=0.21). With all other reactor conditions essentially being the same, the feed mixture was changed to 40%/41%/19%/10% DMK/IPA/H$_2$O/MSO. The reaction product contained 15.8% MIBK and 3.2% DIBK (DIBK/MIBK=0.20). From the data shown in the FIGURE, the DIBK which would have resulted from running the system at higher IPA/DMK conversion would have been 5.4%. Therefore, about a 40% relative reduction in DIBK production was obtained by co-feeding MSO.

Example 6

Approximately 90 cc/hr (LHSV=0.45) of a mixture which was 15%/14%/13%/66% DMK/IPA/H$_2$O/MIBC was fed to 200 cc of Cu-based catalyst at 275° C. and 20 psig. The reactor product contained 49% MIBK and 16.5% DIBK (DIBK/MIBK=0.34). Therefore, with this mixture, significant increases in both MIBK and DIBK production were obtained without reaching unmanageable ratios of DIBK/MIBK.

We claim:

1. A method for the catalytic manufacture of MIBK and DIBK from DMK and/or IPA, and optionally water, while obtaining improved control over the ratio of DIBK to MIBK, comprising reacting, in the presence of an aldol condensation catalyst, a reactant comprising DMK and/or IPA and optionally water, and an effective amount of an additional reactant selected from the group consisting of mesityl oxide (MSO), methyl isobutyl carbinol (MIBC), and mixtures thereof, which results in a deviation in the DIBK/MIBK ratio from that shown in the FIGURE.

2. A method of claim 1 wherein the additional reactant results in a change in the DIBK/MIBK ratio of at least about 5% from that shown in the FIGURE.

3. A method of claim 2 wherein the additional reactant results in a change in the DIBK/MIBK ratio of at least about 10% from that shown in the FIGURE.

4. A method of claim 1 wherein the additional reactant is present in the inlet stream to the reactor in a concentration of at least about 2% by weight.

5. A method of claim 1 wherein the additional reactant is present in the inlet stream to the reactor in a concentration of at least about 5% by weight.

6. A method of claim 1 wherein the additional reactant comprises a mixture of MSO and MIBC.

7. A method of claim 1 wherein at least a portion of the MSO or MIBC is present in the reaction mixture as a result of the reaction of DMK and/or IPA.

8. A method for the catalytic manufacture of MIBK and DIBK from DMK and/or IPA, optionally in the presence of water, while obtaining improved control over the ratio of DIBK to MIBK, comprising reacting, in the presence of an aldol condensation catalyst, a reactant comprising DMK and/or IPA, and an effective amount of an additional reactant selected from the group consisting of mesityl oxide (MSO), methyl isobutyl carbinol (MIBC), and mixtures thereof, which results in a deviation in the DIBK/MIBK ratio from that shown in the FIGURE, and further comprising decreasing or increasing the aldol condensation reaction rate by decreasing or increasing the reaction temperature.

9. A method of claim 8 wherein the ratio of DIBK to MIBK is less than would have been obtained in the absence of the additional reactant.

10. A method of claim 8 wherein the additional reactant comprises a mixture of MSO and MIBC.

11. A method of claim 8 wherein at least a portion of the MSO or MIBC is present in the reaction mixture as a result of the reaction of DMK and/or IPA.

12. A method of claim 1 further comprising changing the DIBK/MIBK ratio by changing the reaction temperature.

13. A method of claim 8 further comprising changing the DIBK/MIBK ratio by changing the reaction temperature.

14. A method of claim 1 wherein the LHSV is about 0.5 to about 1.5.

15. A method of claim 8 wherein the LHSV is about 0.5 to about 1.5.

16. A method of claim 1 wherein hydrogen is in excess.

17. A method of claim 8 wherein hydrogen is in excess.

* * * * *